(12) United States Patent
Rollins et al.

(10) Patent No.: US 11,069,055 B2
(45) Date of Patent: Jul. 20, 2021

(54) PHASE-DECORRELATION OPTICAL COHERENCE TOMOGRAPHY-BASED PARAMETER MEASUREMENT

(71) Applicant: Case Western Reserve University, Cleveland, OH (US)

(72) Inventors: Andrew M. Rollins, Highland Heights, OH (US); Brecken Blackburn, Cleveland, OH (US); Michael Jenkins, Beachwood, OH (US); Shi Gu, Cleveland, OH (US); B J Dupps, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 404 days.

(21) Appl. No.: 15/879,312

(22) Filed: Jan. 24, 2018

(65) Prior Publication Data

US 2018/0211383 A1  Jul. 26, 2018

Related U.S. Application Data

(60) Provisional application No. 62/469,852, filed on Mar. 10, 2017, provisional application No. 62/449,994, filed on Jan. 24, 2017.

(51) Int. Cl.
*G06T 7/00* (2017.01)
*A61B 3/10* (2006.01)
*A61B 5/00* (2006.01)

(52) U.S. Cl.
CPC ............ *G06T 7/0012* (2013.01); *A61B 3/102* (2013.01); *A61B 5/0066* (2013.01); *A61B 5/7203* (2013.01);

(Continued)

(58) Field of Classification Search
CPC ... A61B 2576/02; A61B 3/102; A61B 5/0066; G06T 2207/10101; G06T 2207/30041
See application file for complete search history.

(56) References Cited

U.S. PATENT DOCUMENTS

| | | | |
|---|---|---|---|
| 7,231,243 B2 * | 6/2007 | Tearney | A61B 1/00082 600/407 |
| 7,751,057 B2 * | 7/2010 | Oldenburg | A61B 5/0073 356/497 |

(Continued)

OTHER PUBLICATIONS

Erich Gotzinger et al. "Measurement and imaging of birefringent properties of the human cornea with phase-resolved, polarization-sensitive optical coherence tomography", Journal of Biomedical Optics 9(1), 94-102, 2004 (Year: 2004).*

(Continued)

*Primary Examiner* — Gandhi Thirugnanam
(74) *Attorney, Agent, or Firm* — Tarolli, Sundheim, Covell & Tummino LLP

(57) ABSTRACT

One example includes a scanning system. The system includes a phase-decorrelation optical coherence tomography (PhD-OCT) scanner configured to implement a scanning sequence via an optical signal on a sample medium. The system also includes a scanning controller configured to provide control signals to the PhD-OCT scanner to implement the scanning sequence and to obtain phase and amplitude information associated with a reflected version of the optical signal. The phase and amplitude information can be indicative of microscale dynamics of the sample medium. The scanning controller can also implement an algorithm to calculate a quantitative parameter of the sample medium based on the phase and amplitude information associated with the sample medium.

16 Claims, 6 Drawing Sheets

(52) U.S. Cl.
CPC ......... *A61B 5/7246* (2013.01); *A61B 2576/00* (2013.01); *A61B 2576/02* (2013.01); *G06T 2207/10101* (2013.01); *G06T 2207/30041* (2013.01)

(56) References Cited

U.S. PATENT DOCUMENTS

| | | | | |
|---|---|---|---|---|
| 8,040,608 | B2* | 10/2011 | Evans | G02B 21/0064 359/589 |
| 10,524,663 | B2* | 1/2020 | Boppart | G01B 9/02091 |
| 2002/0183601 | A1* | 12/2002 | Tearney | A61B 1/00082 600/310 |
| 2004/0239946 | A1* | 12/2004 | Kane | G01B 9/0209 356/497 |
| 2006/0072424 | A1* | 4/2006 | Everett | G01B 9/02069 369/112.01 |
| 2006/0164653 | A1* | 7/2006 | Everett | A61B 5/0059 356/479 |
| 2007/0206197 | A1* | 9/2007 | Buckland | A61B 3/102 356/479 |
| 2008/0025570 | A1* | 1/2008 | Fingler | A61B 3/102 382/107 |
| 2009/0005691 | A1* | 1/2009 | Huang | A61B 3/102 600/476 |
| 2010/0238408 | A1* | 9/2010 | Roberts | A61B 3/165 351/212 |
| 2011/0238046 | A1* | 9/2011 | Dick | A61B 3/102 606/5 |
| 2012/0146632 | A1* | 6/2012 | Gleich | A61B 5/0515 324/214 |
| 2012/0179028 | A1* | 7/2012 | Caravan | A61B 5/055 600/420 |
| 2013/0308824 | A1* | 11/2013 | Leung | G06K 9/0061 382/103 |
| 2014/0036272 | A1* | 2/2014 | Nadkarni | G01N 21/4795 356/450 |
| 2014/0236002 | A1* | 8/2014 | Wang | A61B 3/102 600/427 |
| 2015/0133901 | A1* | 5/2015 | Serdarevic | A61F 9/008 606/5 |
| 2015/0216415 | A1* | 8/2015 | Uribe-Patarroyo | A61B 5/0066 600/476 |
| 2015/0223681 | A1* | 8/2015 | Kuranov | G01B 9/02004 600/425 |
| 2015/0371401 | A1* | 12/2015 | Wang | A61B 3/102 348/78 |
| 2016/0220112 | A1* | 8/2016 | Schmoll | A61B 3/102 |
| 2016/0282433 | A1* | 9/2016 | Kannengiesser | G01R 33/4828 |
| 2016/0341539 | A1* | 11/2016 | Adie | G01B 9/02091 |
| 2017/0241765 | A1* | 8/2017 | Adie | G01B 9/02091 |
| 2018/0000339 | A1* | 1/2018 | Hipsley | G16H 50/20 |
| 2018/0211383 | A1* | 7/2018 | Rollins | G06T 7/0012 |
| 2018/0242847 | A1* | 8/2018 | Boppart | G01N 11/00 |
| 2019/0129026 | A1* | 5/2019 | Sumi | G01S 15/8997 |

OTHER PUBLICATIONS

Chang Soo Kim et al., "Imaging and quantifying Brownian motion of micro- and nanoparticles using phase-resolved Doppler variance optical coherence tomography", Journal of Biomedical Optics, vol. 18(3), p. 1-4, 2013 (Year: 2013).*

Jiasong Li et al., "Dynamic optical coherence tomography measurements of elastic wave propagation in tissue-mimicking phantoms and mouse cornea in vivo", Journal of Biomedical Optics 18(12), p. 1-7, 2020 (Year: 2020).*

D Fu et al., "Non-invasive quantitative reconstruction of tissue elasticity using an iterative forward approach", Phys. Med. Biol. 45 (2000), p. 1495-1509 (Year: 2000).*

Brecken J. Blackburn et al. "Monitoring corneal crosslinking with phasedecorrelation OCT (Conference Presentation)", 2018, Proceedings vol. 10474, Ophthalmic Technologies XXVIII, p. 1-2 (Year: 2018).*

* cited by examiner

PHASE-DECORRELATION OPTICAL COHERENCE TOMOGRAPHY-BASED PARAMETER MEASUREMENT

CROSS-REFERENCE TO RELATED APPLICATION

This application claims the benefit of priority from U.S. Provisional Patent Application No. 62/449,994, filed Jan. 24, 2017, entitled OPTICAL COHERENCE TOMOGRAPHY-BASED DIFFUSIVITY AND VISCOSITY MEASUREMENT, and from U.S. Provisional Patent Application No. 62/469,852, filed Mar. 10, 2017, entitled NONINVASIVE ASSESSMENT OF THE CORNEA USING PHASE DECORRELATION OCT, which are each incorporated herein by reference in their entirety.

GOVERNMENT FUNDING

This invention was made with government support under Grant Nos. NIH R01HL083048, NIH R01HL126747, NIH T32EB007509, NIH T32EY007157, NIH C06RR012463, NIH R01EY023381, and NIH IP30EY025585, awarded by the National Institutes of Health (A.M.R.). The United States government has certain rights in the invention.

TECHNICAL FIELD

The present disclosure relates generally to imaging, and more specifically to a phase-decorrelation optical coherence tomography-based parameter measurement.

BACKGROUND

Viscosity is an important property of liquid, measuring resistance to shear or tensile stress. For flowing liquid, such as blood, viscosity connects the pressure gradient to the flow velocity, and influences the shear stress felt by the vessel wall. Maintenance of proper viscosity is also important for the proper function of other bodily fluid, such as mucus or synovial fluid. Under pathological conditions (e.g. inflammation or infection), viscosity of biological fluids can change significantly. Therefore, accurately measuring viscosity of biological samples can lead to better understandings of their normal function, and may lead to better diagnoses of disease.

SUMMARY

One example includes a scanning system. The system includes a phase-decorrelation optical coherence tomography (PhD-OCT) scanner configured to implement a scanning sequence via an optical signal on a sample medium. The system also includes a scanning controller configured to provide control signals to the PhD-OCT scanner to implement the scanning sequence and to obtain phase and amplitude information associated with a reflected version of the optical signal. A quantitative parameter of the sample medium is calculated based on the phase and amplitude information associated with the sample medium, and the quantitative parameter represents microscale dynamics of the sample medium.

Another example includes a method for determining a quantitative parameter of a sample medium of biological tissue. The method includes generating control signals associated with a PhD-OCT scanner to initiate a scanning sequence and implementing the scanning sequence via an optical signal generated by the PhD-OCT scanner on a sample medium over a plurality of scan lines. The method also includes monitoring phase and amplitude information associated with a reflected version of the optical signal. The method also includes implementing an algorithm to calculate a time-dependent complex-valued change associated with an ensemble of samples associated with the sample medium based on the phase and amplitude information to calculate the quantitative parameter of the sample medium. The quantitative parameter represents microscale dynamics of the sample medium.

Another example includes conical measurement system to measure a quantitative parameter of corneal fluid or tissue. The system includes a PhD-OCT scanner configured to implement a scanning sequence via an optical signal on the corneal fluid or tissue of the patient. The system also includes a scanning controller configured to provide control signals to the PhD-OCT scanner to implement the scanning sequence and to obtain phase and amplitude information associated with a reflected version of the optical signal. The scanning system also calculates an apparent diffusion coefficient based on the phase and amplitude information associated with the reflected version of the optical signal.

Another example includes a method for determining a quantitative parameter of corneal medium. The method includes generating control signals associated with a PhD-OCT scanner to initiate a scanning sequence. The method also includes implementing the scanning sequence via an optical signal generated by the PhD-OCT scanner on the corneal medium over a plurality of scan lines. The method also includes monitoring phase and amplitude information associated with a reflected version of the optical signal. The method further includes determining a time-dependent complex-valued change associated with an ensemble of samples associated with the conical tissue or fluid based on the phase and amplitude information and calculating the quantitative parameter of the conical medium based on the time-dependent complex-valued change. The quantitative parameter represents microscale dynamics of the corneal medium.

DETAILED DESCRIPTION

Figure 1:
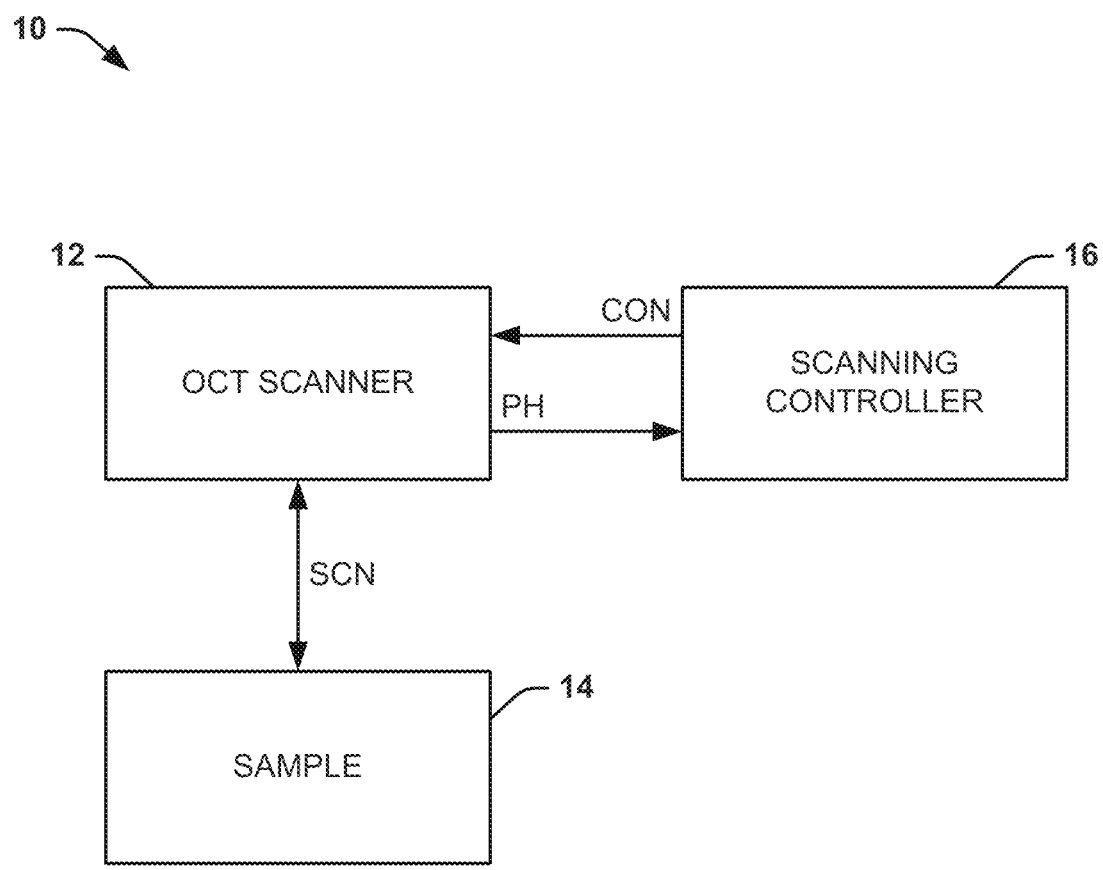
FIG. 1 illustrates an example of a phase-decorrelation optical coherence tomography (OCT) system.

The present disclosure relates generally to imaging, and more specifically to a phase-decorrelation optical coherence tomography-based parameter measurement. As an example, a robust method to measure diffusivity or viscosity of microquantities of biological fluid samples, such as blood and mucus, or of microscale dynamics of biological tissue, could lead to a better understanding and diagnosis of diseases. As described herein, a decorrelation-based method is demonstrated using phase-decorrelation optical coherence tomography (OCT) to measure the microscale dynamics. As described herein, the term "microscale dynamics" is intended to describe motion of microscale scatterers, such as the motion of microscale scatterers in biological tissue (such as lamellar collagen bundles in a cornea) or particle Brownian motion in a fluid (e.g., a biological fluid). As another example, the determination of the microscale dynamics can be analyzed further to determine an indication of viscosity of an associated fluid medium (e.g., a biological fluid) or viscoelasticity of a more solid medium (e.g., biological tissue). Viscoelasticity is the property of a material that exhibits both viscous and elastic characteristics.

The method described herein is sensitivity to nanometer-scale displacement, allows for the measurement to be made in milliseconds, and significantly decreases sensitivity to bulk motion, thereby enabling in vivo and in situ applications. For example, in verification experiments using phantoms of microbeads in 200 μL glycerol-water mixtures, the method described herein demonstrated accurate viscosity measurements, insensitivity to approximately 2 mm/s lateral bulk motion and approximately 0.4 mm/s axial bulk motion over a depth of approximately 400 μm. Additionally, the method measured a significant decrease of diffusivity of soft tissue after formalin fixation, suggesting potential applications in mapping tissue stiffness.

As disclosed herein, a class of methods, named microrheology, can measure a quantitative parameter based on the tracking dynamics of microscale particles in the tissue or liquid sample. These particles undergo random movement from the continuous bombardment of the surrounding medium, also known as Brownian motion. All other things being equal, a less viscous medium will permit more Brownian motion. However, minuscule magnitude of Brownian motion can be difficult to determine. For example, the average displacement of a 1-μm size particle in water may be only 300 nm after approximately 1-second of time, making direct tracking of the particle motion very challenging.

In addition, the PhD-OCT system and method described herein can be implemented for corneal measurement. Therefore, as described previously, the scatterers can correspond to microscale scatterers of a biological tissue (e.g., the cornea), such that the scatterers can correspond primarily to lamellar collagen bundles. As an example, the degree of mobility can be inversely related to the degree of collagen confinement due to crosslinking. Thus, while the term "Brownian motion" may not strictly apply to microscale scatterers in a biological tissue because the OCT signal is likely scattered from the collagen matrix, as opposed to diffusing particles within a liquid matrix, the analysis described herein, derived from coherent dynamic light scattering, assumes Brownian motion. As a result, as described herein, the term "apparent diffusion coefficient" and its derivatives are used to refer to the microscale dynamics corresponding to microscale scatterers of either a biological tissue or a fluid.

FIG. 1 illustrates an example of a PhD-OCT system 10 configured to image a biological tissue or fluid medium to determine a quantitative parameter associated with the biological tissue or fluid medium. As an example, the fluid medium can be a biological fluid that is in vivo or in situ. Therefore, the PhD-OCT system 10 can, for example, be implemented to diagnose diseases or conditions in a medical patient. The PhD-OCT system 10 includes an OCT scanner 12 that is configured to implement a scanning sequence (e.g., a series of A-scans) via an optical signal, demonstrated in the example of FIG. 1 as a signal SCN, across a sample 14 comprising a medium, such as biological tissue or fluid medium. As an example, the sample 14 can correspond to a biological sample (e.g., a human eye), and the biological tissue or fluid medium can be a biological fluid (e.g., conical tissue or fluid). Thus, as used herein, a medium may refer to a solid, a liquid or a substance exhibiting any degree of solid or fluid characteristics. For example, the PhD-OCT system 10 can be implemented in a corneal measurement system configured to measure complex OCT signals and calculate a quantitative parameter (e.g., stiffness and/or viscoelasticity) of a conical tissue of a patient, such as associated with microscale dynamics associated with the corneal tissue (e.g., motion of lamellar collagen bundles). As an example, the PhD-OCT system 10 could be used to provide real-time feedback on the progression of a medical procedure (e.g., laser-assisted in situ keratomileusis (LASIK) surgery) or to screen a patient for corneal defects that could cause complications in a corneal surgery (e.g., LASIK surgery) or other ophthalmological procedure. Other types of fluids (e.g., blood, mucus, synovial) may be used in other examples, and the fluid may not necessarily be limited to biological fluids. Similarly, tissue media are not limited to biological tissues.

The PhD-OCT system 10 also includes a scanning controller 16. Scanning controller can include hardware and/or software (e.g., instructions executable by one or more processor cores) to perform functions disclosed herein. The PhD-OCT system 10 can also employ acquisition circuitry (e.g., an arrangement of one or more amplifiers, filters and an analog digital converter) for providing OCT image data that can be sampled over a period of time and processed by scanning controller 16, as disclosed herein. The OCT image data, for example, represents a plurality of OCT signals (e.g., complex OCT signals) obtained via an optical detector (e.g., a discrete photodetector or an array of photodetectors, such as a camera) based on scanning across a surface of the sample medium. For example, the scanning controller 16 includes controls is configured to provide control signals to the OCT scanner 12 to implement the scanning sequence, such as a series of A-scans. Additionally, the scanning controller 16 includes signal processing (e.g., digital signal processing) to obtain phase and amplitude information from the OCT image data, demonstrated in the example of FIG. 1 as a signal PH, associated with the optical signal SCN.

As an example, the OCT scanner 12 can provide a plurality of A-scans of a given region of the tissue or fluid medium, such as at a high repetition rate (e.g., 50 kHz). The OCT scanner 12 can thus obtain the phase and amplitude information from the OCT image data corresponding to one pixel for analysis, or can obtain the phase and amplitude information from the OCT image data corresponding to multiple pixels of the given region of the tissue or fluid medium (e.g., up to the entire surface of the media) for analysis. As an example, the plurality of A-scans can correspond to multiple sequential measurements in a given scan time that are each evaluated separately and comparatively, or can correspond to a single measurement over the given scan time. By way of example, images can be collected with a linear-K spectral-domain OCT system with a center wavelength of approximately 1310 nm, and axial and lateral resolutions of approximately 10 μm in air. The phase stability can be measured to be approximately 40 mrad, which is the equivalent of axial displacement of approximately 4 nm in air or approximately 3 nm in water. M-mode images of, for example, 25,000 A-lines can be collected to reduce noise by averaging.

The scanning controller 16 can thus implement signal processing (e.g., an algorithm) to calculate a quantitative parameter of the tissue or fluid medium based on the phase and amplitude information PH associated with the optical signal SCN. As an example, the quantitative parameter can correspond to a viscosity of a biological fluid or a viscoelasticity of a biological tissue (e.g., lamellar collagen bundles). For example, the signal processing algorithm can include calculation of a time-dependent complex-valued change, such as a first-order correlation, associated with an ensemble of samples associated with the tissue or fluid medium based on the phase and amplitude information PH. The time-dependent complex-valued change can be used to calculate (e.g., estimate) a mathematical model parameter (e.g., an exponential decay constant) which can be used to calculate an apparent diffusion coefficient of a particle associated with the tissue or fluid medium, and a measure of viscosity or viscoelasticity can be determined from the apparent diffusion coefficient. Thus, the viscosity or viscoelasticity of the fluid or tissue medium can be calculated based on performing the algorithm in response to obtaining the phase and amplitude information PH.

As a further example, the scanning controller 16 includes controls associated with the PhD-OCT system 10 such as controlling one or more control parameters for controlling operating parameters of the OCT scanner 12, such as including parameters of the light source of the OCT scanner (e.g., wavelength, power, etc.) and/or the detector (e.g., detection acquisition rate used for acquiring for the OCT imaging by a detector array). The control parameters and resulting images can be further controlled in response to the user input at scanning controller 16. The controller 16 can also include an output generator to generate a graphical output that can be presented via a display device (not shown). The output generator can provide images in real-time and/or images can be stored in memory.

The phase and amplitude information of the scattered light also enables computation of a first-order $g^{(1)}$ autocorrelation, that can be directly linked to an apparent diffusion coefficient D of the microscale scatterers or particles. If the size and shape of the microscale scatterers or particles are known, the apparent diffusion coefficient D is directly linked to the apparent viscosity of the medium by the Stokes-Einstein equation, as provided below:

$$g^{(1)}(\tau) = \left\langle \frac{\langle E(t)E^*(t+\tau)\rangle_{pixel}}{\sqrt{\langle E(t)E^*(t)\rangle_{pixels}}\sqrt{\langle E(t+\tau)E^*(t+\tau)\rangle_{pixels}}} \right\rangle_{time} = e^{-\Gamma\tau} \quad \text{Equation 1}$$

$$\Gamma = \left(\frac{4\pi n}{\lambda}\right)^2 D \quad \text{Equation 2}$$

$$D = \frac{k_B T}{6\pi \eta R} \quad \text{Equation 3}$$

Where: < > denotes the ensemble average (both in space and in time),
  E is the complex OCT signal (having both real and imaginary parts),
  * denotes complex conjugate,
  n is the refractive index of the solution,
  $\lambda$ is the center wavelength of the light,
  $\Gamma$ is the exponential decay constant,
  D is the apparent diffusion coefficient of the particle,
  $k_B$ is the Boltzmann constant,
  T is temperature,
  R is the radius of the particle, and
  $\eta$ is the dynamic viscosity or viscoelasticity of the sample 14.

Therefore, the PhD-OCT system 10 provides phase and amplitude information that can allow for a very rapid measurement of the apparent diffusion coefficient D of the particle(s) of the sample 14. By comparison, due to the lack of phase and amplitude information, other methods, such as Laser Speckle Rheology (LSR) and diffusion-sensitive OCT (DS-OCT), can be subject to interference. Both LSR and DS-OCT are based on the same principle of speckle formation formed by light interference, which can be very sensitive to particle displacement. For example, the LSR method computes the second order autocorrelation $g^{(2)}$ which is not only affected by particle diffusion, but also by the specific optical setup, and therefore calibrations are utilized to obtain the viscosity or viscoelasticity measurement. In addition, the exponential decay constant $\Gamma$ of the PhD-OCT system 10 can be estimated from the initial linear portion of the decay curve alone, due to the very high sensitivity to displacement of PhD-OCT measurement. For example, the linear initial portion of the decay curve can be interpolated between a first two terms of a Taylor Series expansion of the decay curve. As a result, the PhD-OCT system 10 can provide for reduced measurement time, thus enabling in vivo scanning applications.

Figure 2A:
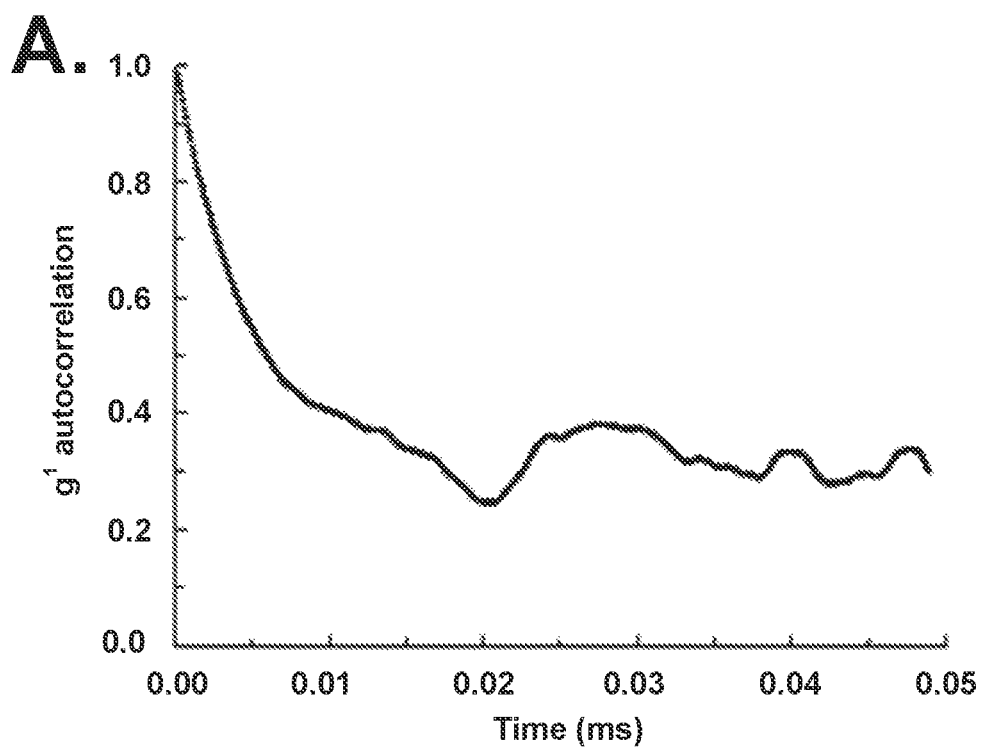
FIGS. 2A-2C illustrate example graphs of a first order autocorrelation.
Figure 2B:
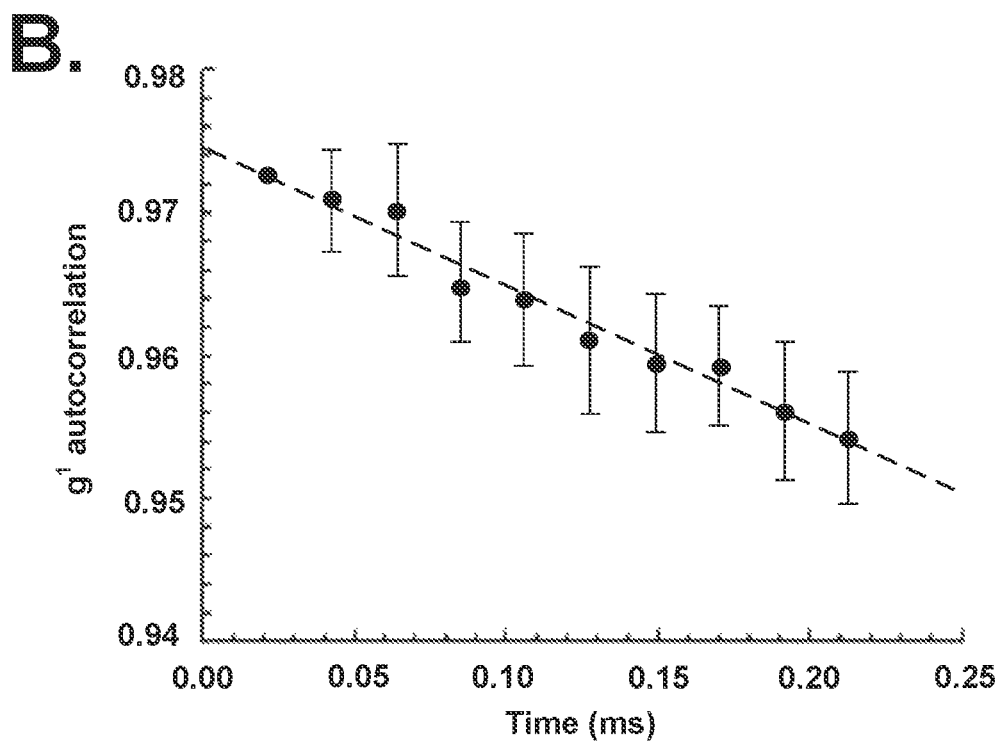

The $g^{(1)}$ autocorrelation can be computed up to, for example, 50 ms delay. To ensure an ensemble average is achieved (e.g., based on Equation 1), correlation can be computed from an image window of, for example, 10×30 pixels (10-pixels axially, and 30-pixels in time). The autocorrelation can be expressed as an exponential curve, and can display motion artifacts (e.g., after approximately 10 ms, such as demonstrated in the example of FIG. 2A). Therefore, the decorrelation curve can be measured to an approximately 1 ms delay, for example. In this range, the decorrelation can be approximately linear. Data from the first approximately 200 μs, for example, can fit to a line to estimate a decay constant (see, e.g., the example of FIG. 2B). With a total recording time of approximately 500 ms, slopes from 500 independent temporal windows can be averaged, and the viscosity can be computed from Equations 2 and 3 (see, e.g., FIG. 2C). A total of six pixels at different depths, for example, (ranging from approximately 50-400 μm below the surface) can be used to compute an average viscosity of the sample 14.

Figure 2C:
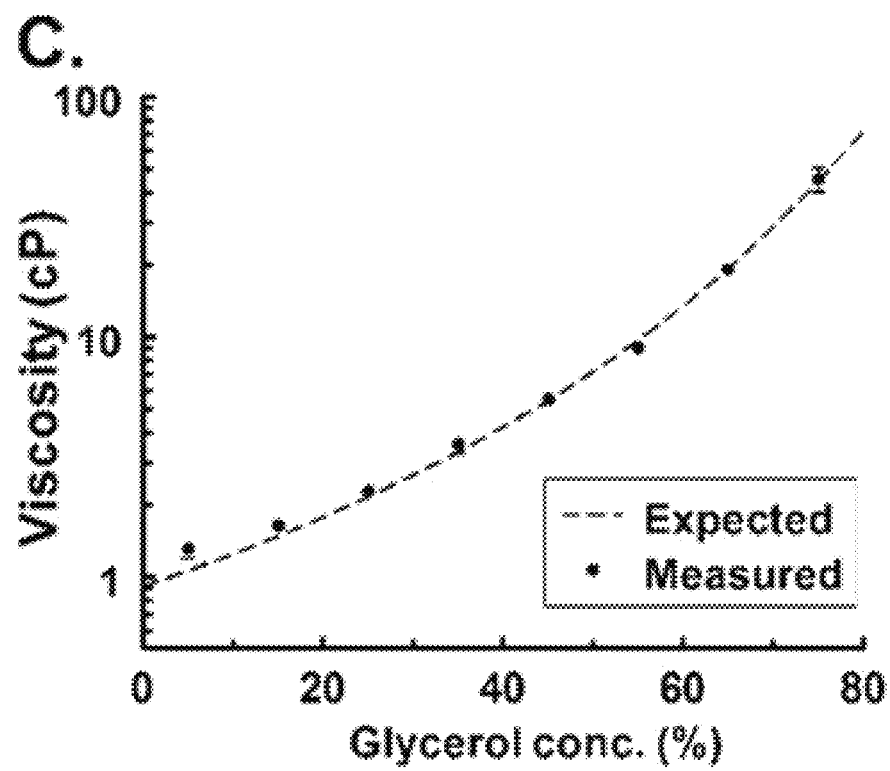

As an example, the diffusivity of the sample 14 can be corrected due to random noise, such as for samples with low diffusivity (high viscosity). The diffusivity of a liquid sample 14, for example, can be calculated from the apparent diffusivity of the liquid sample 14 and the diffusivity of a solid phantom, $D_{corrected} = D_{liquid} - D_{solid}$. After the correction, viscosity can be measured to agree with expected values (FIG. 2C).

Figure 3A:
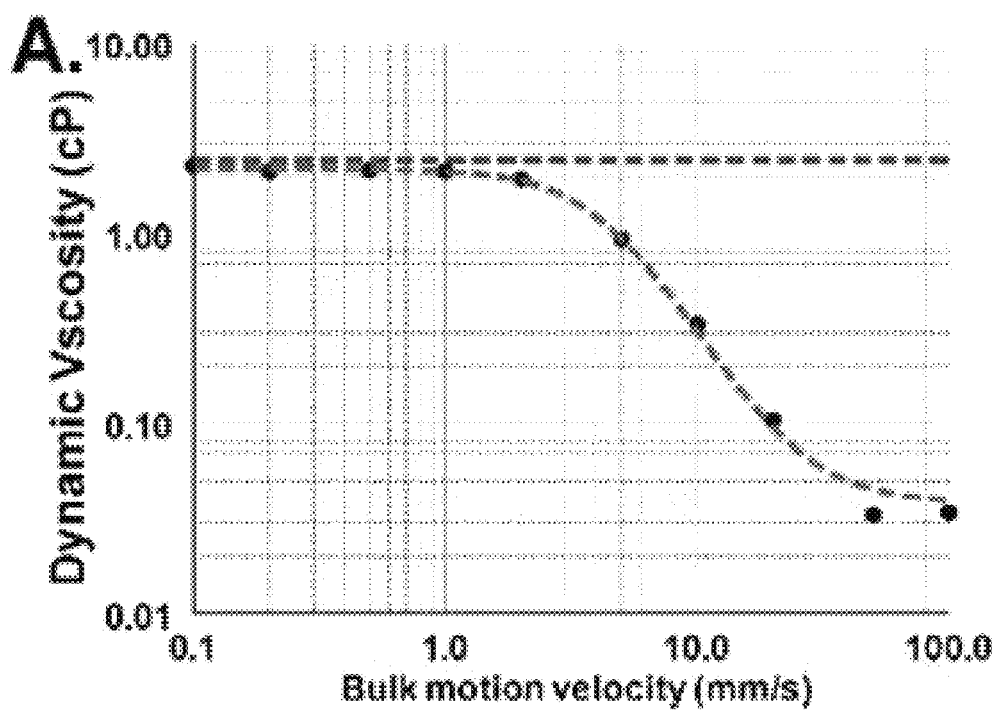
FIGS. 3A and 3B illustrate example graphs of particle velocity.

Using a very short temporal window, for example, the method can be less sensitive to bulk motions, such as lateral or axial motion. As an example, the probe beam of the OCT scanner 12 can be scanned across the sample 14 at various speeds, such as equivalent to moving the sample 14 in the opposite direction. As an example, within a limit of 2 mm/s, the measured viscosity can demonstrate very little sensitivity to lateral motion (see, e.g., FIG. 3A).

Figure 3B:
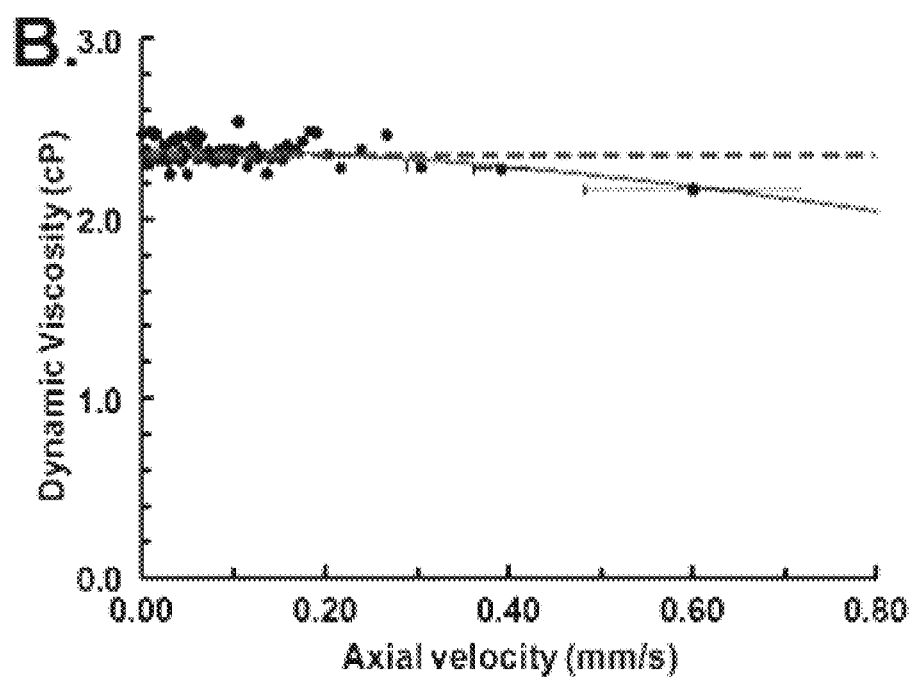

For axial motion, the sample 14 can be manually translated while imaging. The axial velocity can be extracted from the resulting OCT images using Doppler method within a region and time of interest. After diffusivity is computed from each approximately 1-ms segment, results can be ranked based on the average axial velocity and approximately 50 measurements can be binned together to produce an averaged diffusivity and ultimately the viscosity (see, e.g., FIG. 3B). Similar to lateral motion, axial motion can also cause the apparent diffusivity to increase. As an example, the resulting viscosity can be insensitive to up to approximately 0.4 mm/s axial motion (e.g., less than 5% measurement error). Since the decorrelation is phase sensitive, the measurement can be more sensitive to axial motion. To decrease sensitivity to axial motion, as an example, the axial motion can be monitored with Doppler OCT, and data blocks that contain high axial motions can be rejected.

Despite these limitations, approximately 0.4 mm/s can be sufficient for many applications. The density of the particle may not always match that of the solution, but the resulting sedimentation or buoyancy can produce motions much slower than approximately 0.4 mm/s. As an example, in response to samples being measured before and immediately after the sample 14 is stirred, the existence of flows can be confirmed after stirring without affecting the viscosity measurements. This limit of a few mm/s is sufficient to enable viscosity measurement in the presence of slow motions, thereby enabling in vivo applications, or in vitro measurement in samples that are stirred.

As provided by Equation 1, it can be readily demonstrated that common-mode motion does not affect the correlation coefficient. However, non-uniform motion can be indistinguishable from random Brownian motion, and might result in an under-estimation of the viscosity or viscoelasticity of the sample. Because of the short time window, many environmental noise sources, despite being random, can be treated as constant within the approximately 1-ms temporal window, and thus can be effectively ignored by the phase decorrelation method as long as it is slower than a few mm/s. The upper speed limit can roughly correspond to movement of approximately ⅓ of the spot size during the approximately 1-ms temporal window, which is similar to oversampling to obtain high quality Doppler OCT images. As a result, OCT systems with larger spot sizes may be more tolerant to motion.

Therefore, as described herein, phase-sensitive decorrelation OCT is demonstrated to measure dynamic viscosity or viscoelasticity of biological samples. Due to the increased sensitivity to displacement, the measurement can be done in a very short temporal window (1 ms), and random measurement noise can be substantially reduced by averaging given sufficient total imaging time. As an example, the total acquisition time per A-scan can be between approximately 100-500 ms, depending on the viscosity, with low mobility targets possibly requiring a longer imaging time. Furthermore, by utilizing short and independent temporal windows and averaging the resulting diffusivity, motion artifacts can be substantially mitigated, such as to provide a reasonable tolerance to both axial and lateral motion (e.g., roughly in the order of mm/s). Any temporal windows when motion exceeds this limit can be simply discarded, thus rendering the PhD-OCD methodology suitable for in vivo and in situ applications.

As described previously, in addition to monitoring liquid samples, the PhD-OCT method described herein can be used to monitor crosslinking processes in soft tissues. For example, corneal crosslinking (CXL) with riboflavin and UV-A can be implemented to treat corneal ectasia (e.g., keratoconus). Thus, the systems and methods disclosed herein may be used to monitor the progression and acute effects of the crosslinking procedure by computing a measure of microscale dynamics (e.g., apparent diffusion coefficient) of the cornea or a portion thereof based on measured complex OCT signals, such as before, during and after CXL treatment.

As an example, the PhD-OCT system 10 can be implemented as a corneal measurement system that can be implemented to treat a patient prior to, during and/or subsequent to a corneal surgical procedure. Thus, the PhD-OCT system 10 can shift current clinical practice by addressing the persistent need for direct biomechanical measurement of the cornea. For refractive surgery, the PhD-OCT system 10 could enable more direct screening of corneal surgery (e.g., refractive surgery such as a LASIK procedure) candidates for intrinsic biomechanical risk and enhance capabilities for individualized treatment planning through computational models informed by patient-specific biomechanical property measurements. For ectatic disease, the PhD-OCT system 10 could identify keratoconus prior to visual decline to facilitate early stabilization with CXL and provide a means of quantifying CXL treatment efficacy.

The PhD-OCT system 10 can make use of high-speed OCT to quantify random motion within the corneal stroma. For example, in a healthy cornea, the collagen is highly confined by the normal microstructural arrangement, while in a keratoconic cornea, the collagen can be less confined and more mobile. Therefore, a corresponding increase in random motion can be observed. In a cornea treated with crosslinking therapy, the collagen can become more confined and a decrease in random motion can be observed. The measured random mobility corresponding to the microscale dynamics can thus be related to the strength and cohesion of the lamellar collagen and can likely be directly affected by corneal crosslinking. The PhD-OCT system 10 can provide a significant departure from current methods (ORA, CorvisST) and most methods in development (OCT elastography) for determining corneal biomechanical properties, which extract information about elastic parameters of the tissue by inducing bulk quasi-static or dynamic displacements. Apparent diffusion coefficient can represent a different regime of material properties than bulk properties, and may be more sensitive to disease state as opposed to indirect disease manifestations. For example, abnormalities in hydrophilic proteoglycans and other matrix regulating proteins and possible abnormal expression of aquaporin-encoding genes suggest that fluid viscosity of the cornea, rather than just elasticity, may be a key to understanding the mechanisms of keratoconus and its progression. Elastography methods may sometimes access viscosity by applying viscoelastic models to data analysis, but because it is a fundamentally different measurement, the PhD-OCT system 10 may be highly complementary to elasticity-sensitive techniques.

The PhD-OCT system 10 can thus be configured to measure a viscosity or viscoelasticity of the sample 14 corresponding to corneal fluid or corneal tissue of a patient. For example, the PhD-OCT system 10 can be configured to calculate the apparent diffusion coefficient D corresponding to the microscale dynamics of the corneal fluid or tissue, such as to determine the patient's eligibility for a corneal surgical procedure or other ophthalmological procedure and/or to determine whether the patient is recovering properly from a given optical or ophthalmological procedure. For example, the PhD-OCT system 10 can normalize and/or scale the apparent diffusion coefficient D to a predetermined magnitude scale to provide an indication of a treatment option, such as based on the viscoelasticity of the cornea, for the patient. As an example, the treatment option can correspond to a patient's eligibility for the optical or ophthalmological procedure and/or to determine if additional recovery treatment options should be administered to the patient after the optical or ophthalmological procedure. Furthermore, because the PhD-OCT system 10 can be implemented without contact with the patient's eye, the PhD-OCT system 10 can decrease patient discomfort and risk of potential complications, and can increase repeatability of application. As yet another example, the PhD-OCT system 10 can be implemented to profile small biological samples, measure the viscosity or viscoelasticity of a give sample or multiple samples in parallel (e.g., for industrial control testing), assessing the progression of induced lesions (e.g., in response to radio frequency ablation), or any of a variety of other applications.

Figure 4:
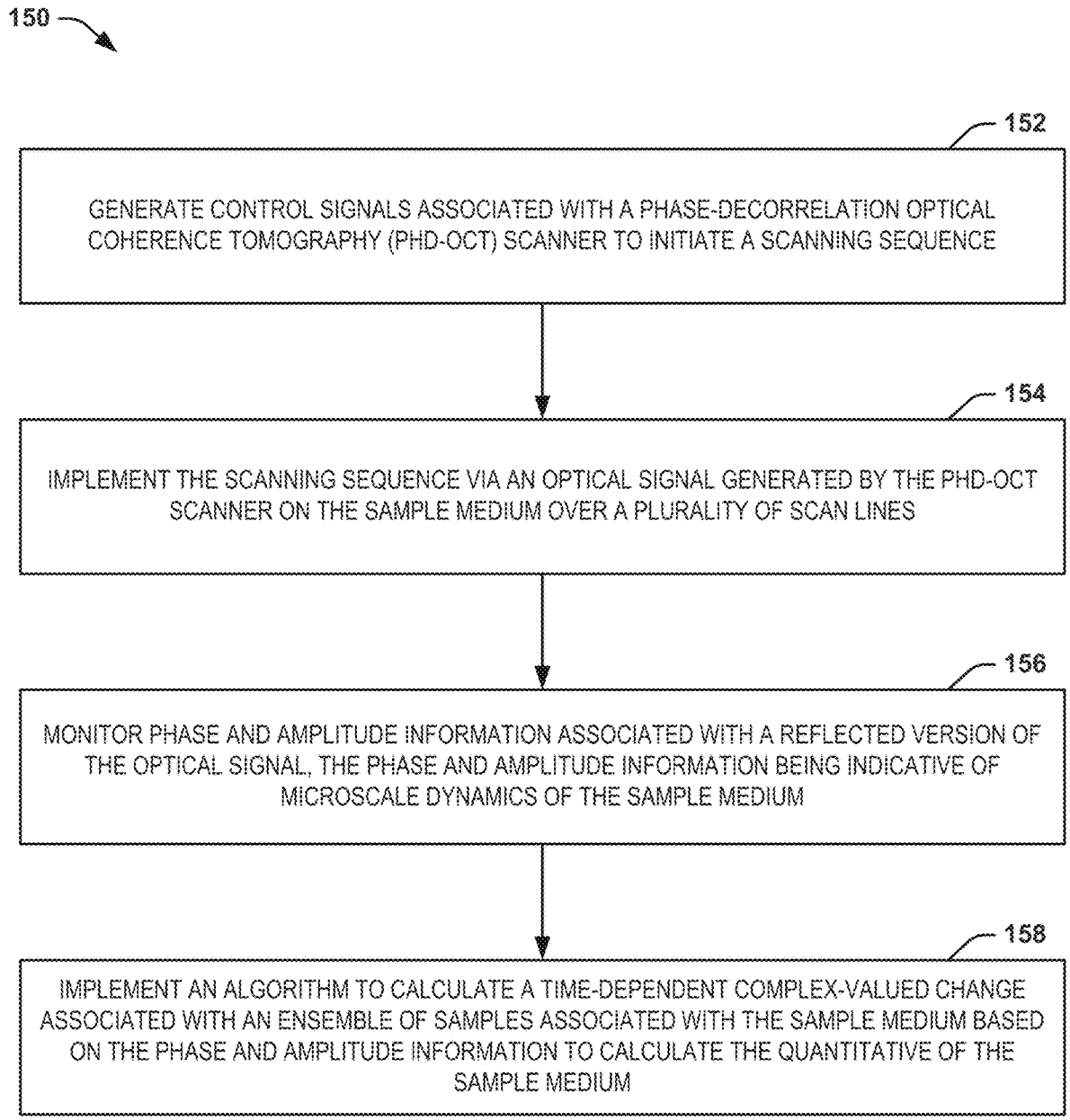
FIG. 4 is a flow diagram illustrating an example method for determining a quantitative parameter of a sample medium.
Figure 5:
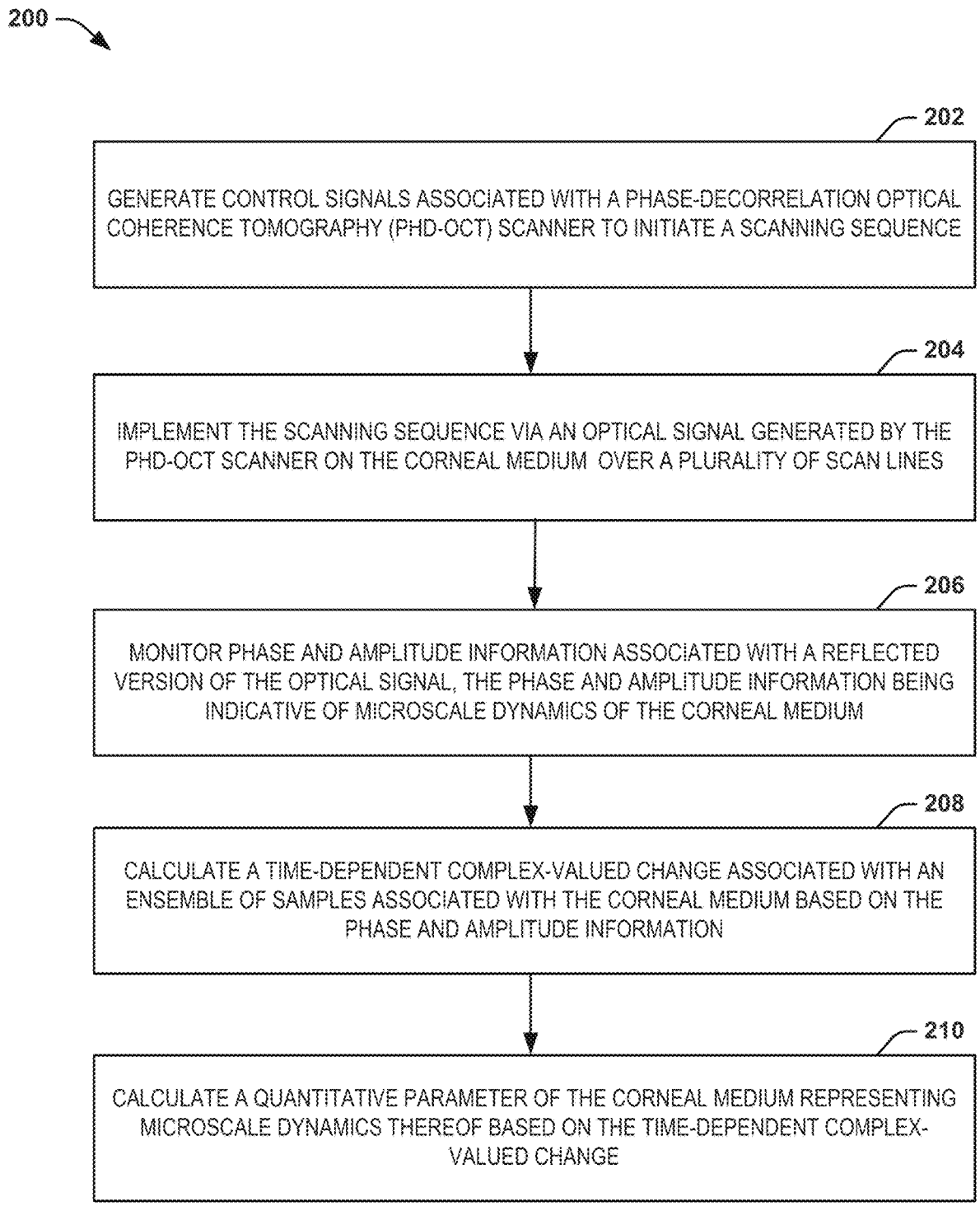
FIG. 5 is a flow diagram illustrating an example method for determining a quantitative parameter of a corneal medium.

In view of the foregoing structural and functional features described above, methods in accordance with various aspects of the present disclosure will be better appreciated with reference to FIGS. 4 and 5. While, for purposes of simplicity of explanation, the method of FIGS. 4 and 5 are shown and described as executing serially, it is to be understood and appreciated that the present disclosure is not limited by the illustrated orders, as some aspects could, in accordance with the present disclosure, occur in different orders and/or concurrently with other aspects from that shown and described herein. Moreover, not all illustrated features may be required to implement method in accordance with an aspect of the present disclosure. Additionally, certain features may be implemented or controlled by one or more processors, such as a controller (e.g., scanning controller 16 of FIG. 1), executing machine-readable instructions.

FIG. 4 illustrates a method 150 for determining a quantitative parameter of a sample medium (e.g., the sample 14) of biological tissue. At 152, control signals (e.g., the control signals CON) associated with a PhD-OCT scanner (e.g., OCT scanner 12) are generated (e.g., via the scanning controller 16) to initiate a scanning sequence. At 154, the scanning sequence is implemented via an optical signal (e.g., the optical signals SCN) generated by the PhD-OCT scanner on the sample medium over a plurality of scan lines. At 156, phase and amplitude information (e.g., the phase and amplitude information PH) associated with a reflected version of the optical signal is monitored. The phase and amplitude information can be indicative of microscale dynamics of the sample medium. At 158, an algorithm to calculate the time-dependent change of the complex-valued PhD-OCT signal associated with an ensemble of samples associated with the sample medium is implemented based on the phase and amplitude information to calculate a measure of viscosity or viscoelasticity of the sample medium (e.g., via the apparent diffusion coefficient D).

FIG. 5 illustrates a method 200 method for determining a quantitative parameter (e.g., a viscoelasticity) of corneal (e.g., tissue and/or fluid) medium of a patient. At 202, control signals associated with a PhD-OCT scanner are generated to initiate a scanning sequence. At 204, the scanning sequence is implemented via an optical signal generated by the PhD-OCT scanner on the corneal tissue or fluid (e.g., the sample 14) over a plurality of scan lines. At 206, phase and amplitude information associated with a reflected version of the optical signal is monitored. The phase and amplitude information may contain information indicative of microscale dynamics of the conical medium. At 208, an algorithm is implemented (e.g., by a processor, such as a controller) to calculate a time-dependent complex-valued change associated with an ensemble of samples associated with the conical medium based on the phase and amplitude information over time. At 210, the quantitative parameter of the corneal tissue or fluid is calculated based on the time-dependent complex-valued change (determined at 208). For example, the quantitative parameter may represent microscale dynamics of the corneal medium, such as corresponding to the apparent diffusion coefficient, as disclosed herein. The calculated quantitative parameter may further be utilized to derive a measure of viscosity or viscoelasticity of the corneal medium.

As can be appreciated by those skilled in the art, portions of the invention may be embodied as a method, data processing system, or computer program product (e.g., a non-transitory computer readable medium having instructions executable by a processor). Accordingly, these portions of the invention may take the form of an entirely hardware embodiment, an entirely software embodiment, or an embodiment combining software and hardware. Furthermore, portions of the invention may be a computer program product on one or more computer-usable storage media having computer readable program code on such media. Any suitable non-transitory computer-readable medium may be utilized including, but not limited to, static and dynamic storage devices, hard disks, optical storage devices, and magnetic storage devices.

Certain embodiments are disclosed herein with reference to flowchart illustrations of methods, systems, and computer program products. It can be understood that blocks of the illustrations, and combinations of blocks in the illustrations, can be implemented by computer-executable instructions. These computer-executable instructions may be provided to one or more processor cores of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in a non-transitory computer-readable medium that can direct a computer or other programmable data processing apparatus (e.g., one or more processing core) to function in a particular manner, such that the instructions stored in the computer-readable medium result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks or the associated description.

From the above description of the invention, those skilled in the art will perceive improvements, changes and modifications. Such improvements, changes and modifications within the skill of the art are intended to be covered by this application, including the appended claims. Accordingly, the invention is intended to embrace all such alterations, modifications, and variations that fall within the scope of this application, including the appended claims. Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, the term "including" means including but not limited to. The term "based on" means based at least in part on. All references, publications, and patents cited in the present application are herein incorporated by reference in their entirety.

What is claimed is:

1. A phase-decorrelation optical coherence tomography (PhD-OCT) scanning system comprising:
   an OCT scanner configured to implement a scanning sequence via an optical signal on a sample medium; and
   a scanning controller configured to provide control signals to the OCT scanner to implement the scanning sequence, the scanning sequence comprising:
   performing an ensemble of scans of the sample medium to obtain complex OCT image data based on a reflected version of the optical signal, wherein the complex OCT image data is representative of a complex OCT signal comprising phase and amplitude information;
   wherein the scanning controller is configured to implement an algorithm to calculate a time-dependent complex-valued change parameter associated with the ensemble of scans based on the phase and amplitude information of the complex OCT signal, wherein the time-dependent complex-valued change parameter characterizes a change of the complex OCT signal as a function of time, the algorithm further to calculate a decay constant based on the time-dependent complex-valued change and to calculate an apparent diffusion coefficient of a particle associated with the sample medium based on the decay constant;
   wherein the scanning controller being configured to calculate a quantitative parameter of the sample medium based on the apparent diffusion coefficient.

2. The system of claim 1, wherein the sample medium is a biological fluid or tissue in vivo or in situ.

3. The system of claim 1, wherein the algorithm further comprises estimating the decay constant based on a substantially linear initial portion of the time-dependent complex-valued change.

4. The system of claim 3, wherein the algorithm further comprises modeling the substantially linear initial portion of the time-dependent complex-valued change based on a first two terms of a Taylor Series expansion of the decay constant.

5. The system of claim 1, wherein the scanning controller includes a signal processing system,
   wherein the phase and amplitude information being determined for at least one time interval from the OCT image data.

6. The system of claim 1, wherein the sample medium is a fluid, wherein the scanning controller is further configured to determine a measure of viscosity for the sample medium based on the apparent diffusion coefficient.

7. A corneal measurement system comprising the scanning system of claim 1, the corneal measurement system being configured to measure an apparent diffusion coefficient of corneal tissue of a patient corresponding to the sample medium.

8. The corneal measurement system of claim 7, wherein the corneal measurement system is configured to normalize and/or scale the apparent diffusion coefficient to a predetermined magnitude scale to provide an indication of viscoelasticity of the cornea.

9. The corneal measurement system of claim 8, wherein the normalized/scaled coefficient has a value that specifies at least one of an indication of corneal defects of the patient, candidacy of the patient for a corneal surgery, and recovery progress of the patient subsequent to a corneal surgery.

10. A method for determining a quantitative parameter of a sample medium of biological tissue, the method comprising:
    generating control signals associated with an OCT scanner to initiate a scanning sequence;
    implementing the scanning sequence via an optical signal generated by the OCT scanner on the sample medium over a plurality of scan lines to obtain an ensemble of scans of the sample medium based on a reflected version of the optical signal from the sample medium over the plurality of scan lines;
    implementing signal processing to generate complex OCT image data associated with the ensemble of scans, wherein the complex OCT image data is representative of a complex OCT signal comprising phase and amplitude information;
    implementing an algorithm to calculate a time-dependent complex-valued change parameter associated with the ensemble of samples based on the phase and amplitude information of the complex OCT signal, wherein the time-dependent complex-valued change parameter characterizes a change of the complex OCT signal as a function of time, the algorithm further to calculate a decay constant based on the time-dependent complex-valued change, and to calculate an apparent diffusion coefficient of a particle associated with the sample medium based on the decay constant; and
    calculating the quantitative parameter of the sample medium based on the apparent diffusion coefficient time, the quantitative parameter representing microscale dynamics of the sample medium.

11. The method of claim 10, further comprising determining the phase and amplitude information for at least one time interval from the OCT image data.

12. The method of claim 10, wherein implementing the scanning sequence comprises implementing the scanning sequence via the optical signal generated by the OCT scanner on corneal fluid or tissue of a patient over the plurality of scan lines.

13. A corneal measurement system to measure a quantitative parameter of a corneal medium, the system comprising:
    an OCT scanner configured to implement a scanning sequence via an optical signal on the corneal medium of the patient; and
    a scanning controller configured to provide control signals to the OCT scanner to implement the scanning sequence, the scanning sequence comprising obtaining an ensemble of scans of the corneal medium to obtain complex OCT image data based on a reflected version of the optical signal, wherein the complex OCT image data is representative of a complex OCT signal comprising phase and amplitude information;
    wherein the scanning controller being configured to implement an algorithm to calculate a time-dependent complex-valued change parameter associated with the ensemble of scans based on the phase and amplitude information of the complex OCT signal, wherein the time-dependent complex-valued change parameter characterizes a change of the complex OCT signal as a function of time, the algorithm further to calculate a decay constant based on the time-dependent complex-valued change, and to calculate an apparent diffusion coefficient based on the decay constant;
    wherein the scanning controller is configured to calculate the quantitative parameter of the corneal medium based on the apparent diffusion coefficient.

14. The system of claim 13, wherein the scanning controller is further configured to normalize and/or scale the apparent diffusion coefficient to a predetermined magnitude scale to provide an indication of viscoelasticity of the corneal medium.

15. A method for determining a quantitative parameter of a corneal medium, the method comprising:

generating control signals associated with an OCT scanner to initiate a scanning sequence;

implementing the scanning sequence via an optical signal generated by the OCT scanner on the corneal medium over a plurality of scan lines to obtain an ensemble of scans of the corneal medium based on a reflected version of the optical signal from the sample medium over the plurality of scans;

implementing signal processing to generate complex OCT image data associated with the ensemble of scans, wherein the complex OCT image data is representative of a complex OCT signal comprising phase and amplitude information;

calculating a time-dependent complex-valued change parameter associated with the ensemble of samples associated with the corneal medium based on the phase and amplitude information of the complex OCT signal, wherein the time-dependent complex-valued change parameter characterizing a change of the complex OCT signal as a function of time;

calculating a decay constant based on the complex-valued change parameter;

calculating an apparent diffusion coefficient based on the decay constant; and calculating the quantitative parameter of the corneal medium representing microscale dynamics of the corneal medium based on the apparent diffusion coefficient.

16. A phase-decorrelation optical coherence tomography (PhD-OCT) scanning system comprising:

an OCT scanner configured to implement a scanning sequence via an optical signal on a sample medium; and a scanning controller configured to provide control signals to the OCT scanner to implement the scanning sequence and to obtain phase and amplitude information associated with a reflected version of the optical signal;

wherein the scanning controller is further configured to implement an algorithm comprising:

calculating a time-dependent complex-valued change parameter associated with an ensemble of samples of the sample medium based on the phase and amplitude information, and calculating a decay constant based on the time-dependent complex-valued change parameter;

calculating an apparent diffusion coefficient; and calculating a quantitative parameter of the sample medium, the quantitative parameter representing microscale dynamics of the sample medium based on the apparent diffusion coefficient.

* * * * *

UNITED STATES PATENT AND TRADEMARK OFFICE
CERTIFICATE OF CORRECTION

| | | |
|---|---|---|
| PATENT NO. | : 11,069,055 B2 | |
| APPLICATION NO. | : 15/879312 | |
| DATED | : July 20, 2021 | |
| INVENTOR(S) | : Andrew M. Rollins et al. | |

It is certified that error appears in the above-identified patent and that said Letters Patent is hereby corrected as shown below:

In the Specification

Please replace second paragraph with the following:
--GOVERNMENT FUNDING
This invention was made with government support under EB007509, HL083048, HL126747, EY007157, RR012463, EY023381, and EY025585 awarded by The National Institutes of Health and 0917940 awarded by the National Science Foundation. The government has certain rights in the invention.--

Signed and Sealed this
Fifth Day of July, 2022

Katherine Kelly Vidal
*Director of the United States Patent and Trademark Office*